United States Patent
Wawrousek et al.

(10) Patent No.: US 10,557,155 B2
(45) Date of Patent: Feb. 11, 2020

(54) METHODS AND SYSTEMS FOR BIOLOGICAL COAL-TO-BIOFUELS AND BIOPRODUCTS

(71) Applicant: The University of Wyoming Research Corporation, Laramie, WY (US)

(72) Inventors: Karen E. Wawrousek, Laramie, WY (US); Patrick Richards, Seattle, WA (US); Alan E. Bland, Laramie, WY (US)

(73) Assignee: The University of Wyoming Research Corporation, Laramie, WY (US)

( * ) Notice: Subject to any disclaimer, the term of this patent is extended or adjusted under 35 U.S.C. 154(b) by 0 days.

(21) Appl. No.: 14/776,272

(22) PCT Filed: Mar. 14, 2014

(86) PCT No.: PCT/US2014/027904
§ 371 (c)(1),
(2) Date: Sep. 14, 2015

(87) PCT Pub. No.: WO2014/152830
PCT Pub. Date: Sep. 25, 2014

(65) Prior Publication Data
US 2016/0032331 A1    Feb. 4, 2016

Related U.S. Application Data

(60) Provisional application No. 61/783,103, filed on Mar. 14, 2013.

(51) Int. Cl.
*C12P 7/64* (2006.01)
*C10L 1/02* (2006.01)

(52) U.S. Cl.
CPC .............. *C12P 7/649* (2013.01); *C10L 1/026* (2013.01); *C10L 2200/0476* (2013.01); *C10L 2270/026* (2013.01); *C10L 2290/26* (2013.01); *C10L 2290/44* (2013.01)

(58) Field of Classification Search
CPC .. C12P 7/649; C10L 1/026; C10L 2200/0476; C10L 2270/026; C10L 2290/26; C10L 2290/44
USPC ........................................................ 435/134
See application file for complete search history.

(56) References Cited

U.S. PATENT DOCUMENTS

| | | |
|---|---|---|
| 3,325,537 A | 6/1967 | Beasley, Jr. et al. |
| 4,516,980 A | 5/1985 | Wheelock |
| 4,760,027 A | 7/1988 | Sublette |
| 5,173,429 A | 12/1992 | Gaddy et al. |
| 5,593,886 A | 1/1997 | Gaddy |
| 5,914,441 A | 6/1999 | Hunter et al. |
| 5,981,266 A | 11/1999 | Srivastava et al. |
| 7,118,896 B2 | 10/2006 | Kalscheuer et al. |
| 7,285,402 B2 | 10/2007 | Gaddy et al. |
| 7,556,094 B1* | 7/2009 | Urynowicz ............. E21B 43/16 166/246 |
| 7,709,624 B2 | 5/2010 | Nakashima et al. |
| 7,832,475 B2 | 11/2010 | Jin et al. |
| 8,127,839 B2 | 3/2012 | Jin et al. |
| 8,268,610 B2 | 9/2012 | Franklin et al. |
| 8,349,587 B2 | 1/2013 | Fischer et al. |
| 8,478,444 B2 | 7/2013 | Fuxman et al. |
| 8,633,012 B2 | 1/2014 | Franklin et al. |
| 2003/0002236 A1 | 1/2003 | Parent et al. |
| 2003/0066322 A1 | 4/2003 | Perriello |
| 2005/0087449 A1 | 4/2005 | Denvir |
| 2006/0172423 A1 | 8/2006 | Van Der Geize et al. |
| 2007/0022122 A1 | 2/2007 | Jin et al. |
| 2008/0050800 A1* | 2/2008 | McKeeman ............. C11C 3/003 435/262.5 |
| 2008/0102515 A1 | 5/2008 | Morales Cerda et al. |
| 2009/0193712 A1 | 8/2009 | Verkade et al. |
| 2010/0081178 A1 | 4/2010 | Roberts et al. |
| 2010/0120104 A1 | 5/2010 | Reed |
| 2010/0257778 A1 | 10/2010 | Gaertner et al. |
| 2011/0146142 A1 | 6/2011 | Lee et al. |
| 2011/0151533 A1 | 6/2011 | Downey et al. |
| 2011/0179699 A1 | 6/2011 | D'addario et al. |

(Continued)

FOREIGN PATENT DOCUMENTS

| | | |
|---|---|---|
| AU | 2014278749 B2 | 3/2018 |
| AU | 2014236594 B2 | 6/2018 |

(Continued)

OTHER PUBLICATIONS

Viana et al., Anaerobic digestion of crude glycerol: a review, Environmental Technology Reviews, vol. 1, No. 1, Nov. 2012, pp. 81-92.*
Kurosawa, et al., "High-cell-density batch fermentation of Rhodococcus opacus PD630 using a high glucose concentration of triacylglycerol production." Journal of Biotechnology 147 (2010) 212-218.
Fuchtenbusch, et al., "Biosynthesis of polyhydroxyalkanoates from low-rank coal liquefaction products by Pseudomonas oleovorans and Rhodoccus ruber." Appl Microbiol Biotechnol (1999) 52: 91-95.
International Patent Application No. PCT/US14/27904; filed Mar. 14, 2014 entitled Methods and Systems for Biological Coal-To-Biofuels and Bioproducts, Search Report dated Aug. 29, 2014. 6 pages.

(Continued)

*Primary Examiner* — Jennifer M. H. Tichy
(74) *Attorney, Agent, or Firm* — Santangelo Law Offices, P.C.

(57) ABSTRACT

Methods and systems for the biological conversion of pretreated or solubilized coal or waste coal into biofuels. Coal (10) may be pretreated perhaps in a pretreatment reactor (13). Pretreated coal or even solubilized coal may be introduced into a processing reactor such as a bioreactor (16) containing a plurality of microorganisms (9) such as oleaginous microorganisms which can convert at least some of the pretreated or solubilized coal into lipids (19) or biomass (18), which then may be used directly or as a precursor for various products such as biofuels, feedstock, or the like.

10 Claims, 2 Drawing Sheets

(56) References Cited

U.S. PATENT DOCUMENTS

| | | |
|---|---|---|
| 2011/0207061 A1 | 8/2011 | Cantwell |
| 2011/0225787 A1 | 9/2011 | Moulijn et al. |
| 2011/0225878 A1 | 9/2011 | Moulijn |
| 2011/0244532 A1 | 10/2011 | Hu et al. |
| 2011/0277991 A1 | 11/2011 | Toledo et al. |
| 2011/0287497 A1 | 11/2011 | Holtzapple et al. |
| 2012/0003705 A1 | 1/2012 | Jin et al. |
| 2012/0064609 A1 | 3/2012 | Clement et al. |
| 2012/0064622 A1 | 3/2012 | Fischer et al. |
| 2012/0085705 A1 | 4/2012 | Theodore et al. |
| 2012/0110898 A1 | 5/2012 | Malm et al. |
| 2012/0142979 A1 | 6/2012 | Keasling et al. |
| 2012/0244585 A1 | 9/2012 | Kale et al. |
| 2012/0247763 A1 | 10/2012 | Rakitsky et al. |
| 2012/0264983 A1 | 10/2012 | Hu et al. |
| 2013/0065285 A1 | 3/2013 | Sefton |
| 2013/0078690 A1 | 3/2013 | Reed |
| 2013/0089899 A1 | 4/2013 | Kurek et al. |
| 2013/0130341 A1 | 5/2013 | Liao et al. |
| 2013/0137887 A1 | 5/2013 | Kurosawa et al. |
| 2013/0149755 A1 | 6/2013 | Reed et al. |
| 2013/0189739 A1 | 7/2013 | Jin et al. |
| 2013/0189763 A1 | 7/2013 | Dalla-Betta et al. |
| 2016/0030884 A1 | 2/2016 | Wawrousek et al. |

FOREIGN PATENT DOCUMENTS

| | | |
|---|---|---|
| EP | 0218958 A3 | 4/1987 |
| EP | 2025755 A1 | 2/2009 |
| EP | 2546352 A1 | 1/2013 |
| WO | 9118661 | 12/1991 |
| WO | 2007022122 A2 | 2/2007 |
| WO | 2007109066 A1 | 9/2007 |
| WO | 2008040365 A1 | 4/2008 |
| WO | 2008128331 A1 | 10/2008 |
| WO | 2008151149 A2 | 12/2008 |
| WO | 2009002772 A3 | 12/2008 |
| WO | 2010120939 A2 | 10/2010 |
| WO | 2011006019 A2 | 1/2011 |
| WO | 2011014507 A1 | 2/2011 |
| WO | 2011056183 A1 | 5/2011 |
| WO | 2011071553 A1 | 6/2011 |
| WO | 2011075163 A1 | 6/2011 |
| WO | 2011130407 A1 | 10/2011 |
| WO | 2011133218 A1 | 10/2011 |
| WO | 2011139804 A2 | 10/2011 |
| WO | 2011149956 A2 | 12/2011 |
| WO | 2012154329 A1 | 11/2012 |
| WO | 2013006912 A1 | 1/2013 |
| WO | 2013074371 A2 | 5/2013 |
| WO | 2013082309 A1 | 6/2013 |
| WO | 2013148348 A1 | 10/2013 |
| WO | 2013177471 A2 | 11/2013 |
| WO | 2014152830 A1 | 9/2014 |
| WO | 2014152830 A4 | 9/2014 |
| WO | 2014200598 A2 | 12/2014 |
| WO | 2014200598 A3 | 12/2014 |

OTHER PUBLICATIONS

International Patent Application No. PCT/US14/27904; filed Mar. 14, 2014 entitled Methods and Systems for Biological Coal-To-Biofuels and Bioproducts, Written Opinion dated Aug. 29, 2014. 8 pages.

International Patent Application No. PCT/US14/29843; filed Mar. 14, 2014 entitled Conversion of Carbon Dioxide Utilizing Chemoautotrophic Microorganisms Systems and Methods, Search Report dated Feb. 2, 2015. 5 pages.

International Patent Application No. PCT/US14/29843; filed Mar. 14, 2014 entitled Conversion of Carbon Dioxide Utilizing Chemoautotrophic Microorganisms Systems and Methods, Written Opinion dated Feb. 2, 2014. 6 pages.

International Patent Application No. PCT/US14/29843, filed Mar. 14, 2014, "Conversion of Carbon Dioxide Utilizing Chemoautotrophic Microorganisms Systems and Methods," International Preliminary Report on Patentability, dated Jan. 5, 2016, 99 pages.

Australian Patent Application No. 2014236594. First Named Inventor: Wawrousek. Examination report No. 1, dated Aug. 3, 2017. 6 pages.

Australian Patent Application No. 2014236594. First Named Inventor: Wawrousek. Examination report No. 2, dated Apr. 18, 2018. 2 pages.

Australian Patent Application No. 2014236594. First Named Inventor: Wawrousek. Notice of Acceptance dated May 22, 2018. 3 pages.

European Patent Application No. 14769071.3. First Named Inventor: Wawrousek. Extended European Search Report dated Sep. 20, 2016. 10 pages.

European Patent Application No. 14810529.9. First Named Inventor: Wawrousek. Extended European Search Report dated Jun. 21, 2017. 14 pages.

European Patent Application No. 14810529.9. First Named Inventor: Wawrousek. Communication Report dated Apr. 3, 2018. 4 pages.

U.S. Appl. No. 14/776,611. First Named Inventor: Wawrousek. Office Action dated Feb. 23, 2018. 11 pages.

U.S. Appl. No. 14/776,611, filed Sep. 14, 2015. First Named Inventor: Wawrousek. Notice of Allowance dated Apr. 8, 2019. 7 pages.

U.S. Appl. No. 14/776,611, filed Sep. 14, 2015. First Named Inventor: Wawrousek. Office Action dated Dec. 14, 2018. 7 pages.

Korean Patent Application No. 10-2015-7029493, English Translation of the Office Action dated Apr. 9, 2019. 4 pages.

* cited by examiner

US 10,557,155 B2

METHODS AND SYSTEMS FOR BIOLOGICAL COAL-TO-BIOFUELS AND BIOPRODUCTS

PRIORITY CLAIM

This application is the United States National Stage of International PCT Patent Application No. PCT/US2014/027904 filed Mar. 14, 2014 which claims priority to and the benefit of U.S. Provisional Patent Application No. 61/783,103 filed Mar. 14, 2013, each application is hereby incorporated herein by reference in its entirety.

GOVERNMENT LICENSE RIGHTS

This application relates to work performed under U.S. DOE Cooperative Agreement DE-FC26-08NT43293. The U.S. government may have certain rights in this inventive technology, including "march-in" rights, as provided for by the terms of U.S. DOE Cooperative Agreement DE-FC26-08NT43293.

FIELD OF THE INVENTION

The present invention relates to methods and systems for the conversion of coal, including waste coal, to liquids or gaseous biofuels. This process may occur in simple reactors, perhaps at near-ambient temperature and pressure, and may not rely on expensive catalysts. These improvements are expected to drastically reduce the cost of coal-to-liquid fuels. Through perhaps the use of oleaginous bacteria, the present invention may provide systems and methods that can be used to convert coal, including waste coal, into biofuels, such as but not limited to biodiesel, methane, or the like.

BACKGROUND

Coal is a low cost fuel that is abundant in the United States, as well as other countries around the world. Both the price and availability of coal make it an attractive fuel for large, stationary operations such as power plants. However, coal suffers from many draw backs as a fuel. Compared to petroleum or natural gas, coal has a relatively low energy content, as well as a high moisture content, which reduces net energy conversion. The solid nature of coal may also make it difficult to transport perhaps when it is not near rail lines (e.g., not pipeline compatible), and it is not compatible with conventional engines. Further, coal may contain a significant mass fraction which is not fuel and can result in air pollution in the form of SOx, NOx, mercury, particulate, and other unwanted compounds. One way to add value to coal feedstocks, perhaps as well as address some of the pollution problems related to coal, may be to convert the solid coal into a liquid or gaseous fuel. This may be achieved through coal-to-liquid (CTL) technologies or perhaps even conversion to methane.

Coal is a low cost and abundant energy source which is vital to the United States. However, coal suffers from certain draw backs, such as the inability to use coal directly as a transportation fuel and perhaps the significant amount of pollutants that are released from the combustion of coal. Coal-to-liquid fuel and coal-to-methane technologies may allow coal to be converted to value-added products. However, these technologies currently are inefficient and economically uncertain.

Conventional CTL technologies may be based upon direct liquefaction or the Fischer-Tropsch reaction, in which coal may be gasified and subsequently reacted to produce olefins and paraffin. These technologies have existed for more than 80 years and have been shown to be operable at an industrial scale. CTL technologies have been used successfully in places such as South Africa, where coal is abundant but petroleum supplies can be tenuous. However, these technologies have never enjoyed wide popularity perhaps due to their inefficiency, environmental concerns, and uncertain economics. Some coal-to-liquid technologies may only be capable of producing 1-2 barrels of synthetic petroleum per ton of coal, and may require catalysts in addition to high temperatures and even high pressures for the reaction. The inefficiencies of these processes may result in a very large environmental footprint, perhaps with a typical release of over about 60% of the carbon input as $CO_2$.

A factor that may have kept CTL technologies from gaining wide popularity may be the economic uncertainty from volatile oil prices. Current outlook projects that CTL may be economically viable perhaps when oil prices are greater than about $60 per barrel. Therefore, these technologies may be attractive with current oil prices (>about $100/bbl). However, CTL plants may require larger capital costs, and oil prices have dropped below the about $60/bbl mark as recently as 2009.

Another unconventional method of utilizing coal has been the production of biogenic methane. Microorganisms produce methane from coal under natural conditions in many coal formations around the world. In recent years, there has been significant interest in technologies for enhanced production or collection of biogenic methane.

Enhanced biogenic methane production may be achieved in the laboratory, and pilot scale experiments are currently under way such as in the Powder River Basin of Wyoming, China, Australia,—and elsewhere—to determine if these technologies are scalable and economically viable. While coal-to-biogenic methane processes may produce a value-added product from coal, methane prices are currently well below those of transportation fuels. If the United States continues to experience the current low methane prices, these technologies that produce enhanced biogenic methane may not be an attractive use for coal.

DISCLOSURE OF INVENTION

The present invention provides methods and systems for producing biofuel from coal. Various embodiments include pretreating coal, bioreacting coal with at least one type of coal-utilizing bacteria, generating biomass and lipids from said bioreaction and converting said lipids into biofuel. In embodiments, products and by-products of the system may be recycled back into the system or may be used to produce methane or the like. Naturally, further objects, goals and embodiments of the inventions are disclosed throughout other areas of the specification and claims.

MODE(S) FOR CARRYING OUT THE INVENTION

Figure 1:
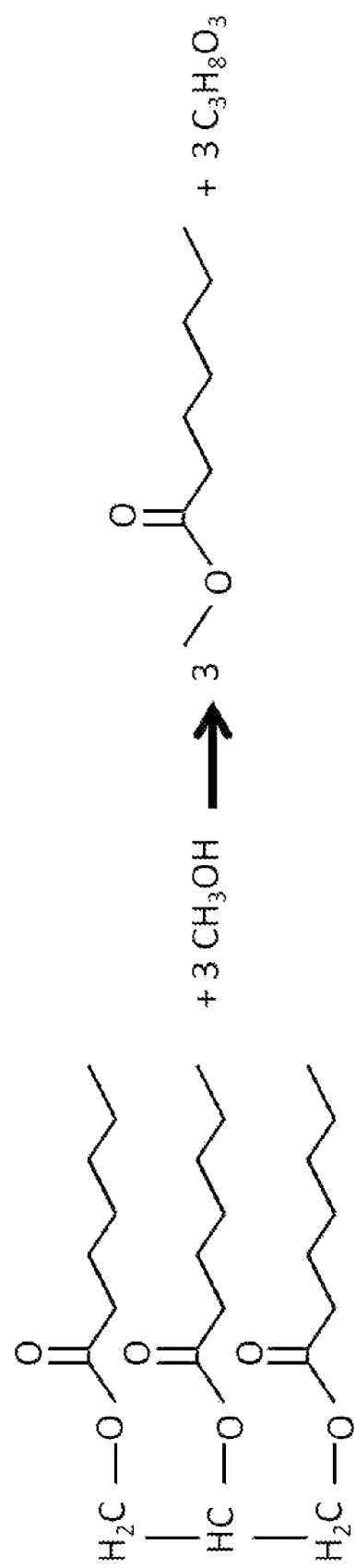
FIG. 1 shows transesterification of a TAG with methanol to produce biodiesel and glycerol. The fatty acid side chains depicted above are shortened for clarity. FAMEs or even target TAGs may have fatty acids side chains in the range of $C_{15-25}H_{28-48}O_2$.

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

The present invention, in embodiments, relates to a biological production of a liquid replacement fuel from a low-rank coal feedstock. In embodiments, the present invention may provide pretreated or solubilized coal processed by microorganisms into fuel precursor molecules. Microorganisms may be harvested, perhaps fuel precursors may be extracted from the cells, and may even be reacted chemically to produce biodiesel, or the like.

Although coal may be energy dense and even carbon rich, it may make a poor feed stock for microorganisms perhaps due to large molecular size, structural heterogeneity, and even recalcitrant functionalities. It has been established that certain microorganisms can grow on coal, but that growth may often be slow and may not fully utilize coal. The microbial conversion of native coal into biodiesel may be impractical due to the aforementioned slow growth, perhaps as well as the fact that few microorganisms accumulate significant amounts of useful fuel precursor molecules. However, a variety of pretreatments, perhaps even ex situ pretreatments, may make coal more accessible to microbial utilization. Pretreatments may consist of an alkali, acid, solvent, oxidizing agent, or any combination of these, or the like. Exposure of coal to said pretreatment agents may solubilize the coal, which in turn can increase the bioavailability. Pretreated coal may not have been well characterized, and a composition may depend on a composition of the coal and/or even the type and concentration of pretreatment. Significant interest may have been generated relating to the microbial utilization of coal, perhaps including processes which may convert coal to methane, hydrogen, and alcohols. Some pretreatments may be effective at enhancing the production of biogenic methane from coal, perhaps including the pretreatment method as discussed in PCT Pub. Nos. WO2007/022122 (discussing in-situ pretreatment of formations), WO2011/133218, WO2011/071533, WO2011/075163, and WO2013/177471, U.S. Pat. Nos. 8,127,839, 7,832,475, 7,556,094, and US Patent Pub. No. US2009/0193712, each hereby incorporated by reference herein. However, there is a need to provide methods and systems for conversion of coal into biodiesel or similar products perhaps through the use of microorganisms or the like.

Bacteria produce a number of potential fuel precursor molecules, such as diacylglycerols (DAGs), which may be a component of cell membranes. Certain species of oleaginous bacteria, such as members of the genus *Rhodococcus*, may have been shown to accumulate large amounts of triacylglycerols (TAGs), under certain conditions. TAGs may be neutral, hydrophobic, and even energy storage compounds consisting of three fatty acids bound to a glycerol backbone. They may have a similar molecular structure to many plant-based oils. DAGs, TAGs, and other related compounds (hereafter collectively referred to as "lipids") can be easily converted into biodiesel through a transesterification with a short chain alcohol (FIG. 1). When methanol may be used for the transesterification reaction, the resulting products may be fatty acid methyl esters (FAMEs), of which conventional biodiesel may be comprised. The production of biodiesel from bacterial lipids could be technologically similar to the production of biodiesel from plant oils. Further, bacteria in the genus *Rhodococcus* or other oleaginous microorganisms have been shown to be capable of growth on at least about 164 different carbon sources, perhaps including low-rank coal liquefaction products. Bacteria from the genus *Rhodococcus* may be used in embodiments of the present invention perhaps because of their ability to utilize a large range of carbon sources (e.g., including coal liquefaction products), and even because they have been shown to accumulate large amounts of TAGs under certain conditions. Any biomass generated by a process that cannot be converted into biodiesel may be fed into an anaerobic digester for the production of methane. Glycerol produced during biodiesel processing may also be fed into the anaerobic digester, perhaps if it is economical. Depending upon the amount of methane produced, methane could be sold, used within the process to generate heat or electricity, or perhaps even used to produce methanol for biodiesel production or the like. In embodiments, methanol may be directly or even indirectly produced from said non-lipid biomass. Aside from some amount of waste water and perhaps even unreacted coal, there may be very little waste generated in this process.

In embodiments, the present invention may provide a series of separate vessels for each of the following, perhaps in any process order: coal pretreatment reactor (13); bioreactor (16); biomass harvesting and/or separation of lipids from other biomass (17); biodiesel production (22); and perhaps even methane production in an anaerobic digester (20), or the like. Of course any single process may be used individually or in any combination thereof. Separate vessels may not be needed and some or all processes may be achieved in at least one or more reactors or the like. Various inputs and outputs of a system may generally relate to each process or step. However, actual inputs and outputs may not be utilized if processes are achieved in a single or fewer vessels or the like. Thus, inputs and outputs may relate to the process and may or may not relate to actual physical movement of various elements. The pretreatment reactor could be able to accept coal, coal fines, or other waste coal, and could have a system for the addition of alkali and acid. In this reactor, an aqueous slurry of coal, coal fines, or other waste coal could be reacted with alkali perhaps for a defined period of time, after which acid could be added perhaps to return the pH to a circum-neutral level. Solubilized coal from a pretreatment reactor could be pumped into a bioreactor, where a bacterial culture may be maintained. Water insoluble fractions could be removed from a pretreatment reactor separately or could be removed from the liquid stream using filtration, centrifugation, flotation, settling or other techniques known in the art. Once the solubilized coal may be sent to the bioreactor, a seed culture of at least one type of coal-utilizing bacteria could be introduced. Combinations of different types of bacteria and other types of bacteria may be used in various embodiments. The culture could be allowed to grow to a defined biomass concentration, perhaps at which time nitrogen starvation or other nutrient deprivation methods or even cell stress methods could be used to cause a slowing or even cessation of cell division while triggering the cells to accumulate lipids, e.g., TAGs or the like. After a defined amount of time or even at a defined lipid concentration, the bacteria could be harvested from the bioreactor. Alternately, if the microorganisms present in the reactor are engineered for continuous lipid production, the culture could be grown in a steady state perhaps with continuous removal of culture.

The bacteria could be disrupted by chemical or physical means, and perhaps the lipids may be separated from the residual biomass. The lipids could be brought to a biodiesel production unit, in which they may be transesterified perhaps with methanol, and biodiesel and glycerol can be collected and even separated. A non-lipid biomass ("bioresidue") could be taken from a separation step and may be fed into an anaerobic digester perhaps to produce methane. Perhaps depending on the relative values of glycerol and methane, glycerol may also be fed into the anaerobic digester for methane production.

Many variants of the present invention are expected. There are several possible coal pretreatment methods, including, but not limited to, the use of alkalis, acids, solvents, and perhaps even oxidizing agents as discussed herein. Many different types of microorganisms may be used, including, but not limited to, members of the genera *Rhodococcus, Streptomyces, Acinetobacter, Pseudomonas, Nocardia, Mycobacterium, Gordonia, Dietzi*, other oleaginous microorganisms, other microorganisms that grow on coal, or any combination thereof, and the suitability of specific types or consortia of microorganisms may be determined empirically. The genera mentioned may accumulate TAGs, may grow on coal, or even both. Microorganisms used may or may not be genetically modified for enhanced growth on solubilized coal, enhanced production of lipids, or enhanced accumulation of lipids. Selected microorganisms may be grown on solubilized coal or both solubilized coal and an organic or inorganic carbon substrate. A bioreactor in which the bacteria may be grown may be a stirred tank bioreactor, air lift bioreactor, or other forms of bioreactor perhaps known in the art or the like. Cells may be harvested by filtration, centrifugation, or even other common methods. Lipids may be extracted from the bacterial cells perhaps by physical methods, such as, but not limited to, sonication, changes in temperature and/or pressure, by chemical methods, including, but not limited to, solvent extraction, electrical, or even by other methods known to the art, or the like.

Products other than biodiesel can also be generated using embodiments of the present invention, such as jet fuel and other fuel replacements, or the like. Alternatively, embodiments of the present invention may be used to generate salable chemicals.

Lipids from the bacteria can be separated from a non-lipid biomass residue for a variety of purposes, including, but not limited to conversion to biodiesel or other biofuels or creation of a lipid slurry used for co-firing or a direct fuel replacement, or fuel blending agent, or the like. Biomass can be used directly for combustion, thermochemical conversion, or the like.

Non-lipid biomass residue may be processed for the generation of methane, and may even be recycled to use as nutrients in the coal-consumption bioreactor. Alternatively, non-lipid biomass can be used as animal feed, aquatic feed, or the like.

Figure 2:
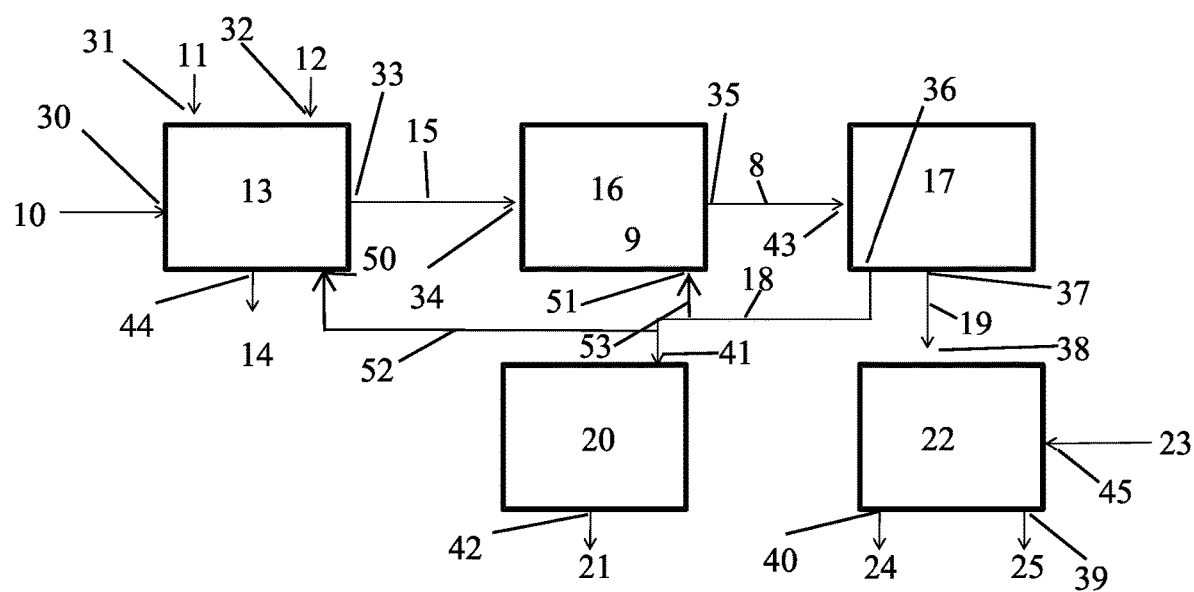
FIG. 2 shows process flow diagram of various embodiments of the present invention.

As can be understood from FIG. 2, coal (10) such as coal fines, waste coal, low grade coal, or any kind of coal, or combinations thereof may be introduced into a pretreatment reactor (13) perhaps by a coal input (30). Acid (11) or any other treatment element may be introduced into a pretreatment reactor perhaps by an acid input (31). Alkali (12) or any other treatment element may be introduced into a pretreatment reactor perhaps by an alkali input (32). An waste removal element (44) such as but not limited to an insoluble fractions removal element may be used to remove waste (14) or other excess components from the pretreatment reactor such as waste water, unreacted coal, liquids, or the like. A pretreatment reactor may provide solubilized or even pretreated coal (15) perhaps by a solubilized or pretreated coal output (33). Solubilized or even pretreated coal (15) may be processed (which may be in a same treatment system(s) or even in a different system) perhaps by a solubilized or even pretreated coal input (34) into a bioreactor (16). Pretreated or solubilized coal or the like may be combined with at least one type of coal-utilizing bacteria (9) in a bioreactor (16). As a result, a bioreactor may generate biomass (8) perhaps by a biomass output (35). Biomass may be processed such as by harvesting, separating, or the like perhaps in a biomass harvesting and separation vessel (17) (which may be in a same treatment system(s) or even in a different system) and perhaps by a biomass input (43). A biomass harvesting vessel or process may generate lipids (19) perhaps by a lipid output (37). A biomass harvesting vessel or process may generate non-lipid biomass (18) perhaps by a non-lipid biomass output (36). Lipids may be processed perhaps by a lipid input (38) for biofuel production perhaps in a biofuel production unit (22) (which may be in a same treatment system(s) or even in a different system). Methanol (23) may be introduced to lipids (19) perhaps by a methanol input (45). Biofuel production perhaps in a biofuel production unit may generate glycerol (25) perhaps by a glycerol output (39) and may even generate a biofuel (24) perhaps by a biofuel output (40). In embodiments, non-lipid biomass (18) may be fed (52) into a pretreatment process or reactor (13) perhaps by a non-lipid biomass input (50). In other embodiments, non-lipid biomass may be fed (53) into a bioreactor perhaps by a non-lipid biomass input (51). Non-lipid biomass (18) may be processed anaerobically perhaps in an anaerobic digester (20) perhaps by a non-lipid biomass input (41) (which may be in a same treatment system(s) or even in a different system) to produce methane (21) perhaps by a methane output (42). Any of the various inputs and outputs and any of the various method steps may be substantially of a specific type of element (e.g., substantially lipids, substantially non-lipid biomass, substantially biomass, etc.).

This process could have a substantial impact on coal-producing areas. A vibrant coal-to-liquids industry could diversify the economy perhaps by increasing the number of potential export products to include liquid fuel, and also potentially other chemical feed stocks or the like. These products could be value-added, relative to the coal, thereby allowing coal-producing areas to realize greater gains from their extractive industries. In addition, this process could be used to create value from otherwise unusable feed stocks, such as coal that may be too low grade or even too deeply buried to be economically mined. This process could also use waste products, such as waste coal fines, as a feedstock or the like.

Coal-to-biodiesel could also have a number of environmental benefits and could help to move the energy sector one step closer to the vision of "clean coal". Since the coal may be reacted in a liquid system, rather than combusted, the release of SOx, NOx, ash, and toxic metals into the air can be minimized. These materials can be collected and even disposed of more easily from a liquid system and perhaps at a significantly lower cost compared to capture from flue gas. If waste products, such as coal fines or the like, may be used as a feed stock, the amount of waste generated prior to combustion and even the cost of disposal of that waste can be significantly reduced. This could include wastes from the coal mine or even coal fines from a power plant, transloading facility, or any other layout which may have waste fines for disposal. It may also be possible to collect potentially useful fractions of the coal ash in these processes.

Additionally, embodiments of the present invention may serve as a proof-of-concept for bacterial conversion of low-rank coal to value-added products. Successful biodiesel production may pave the way for future projects involving microbial conversion of coal to other petroleum replacement products or the like.

Clauses

Clause 1a. A method for producing biofuel from coal comprising the steps of:
pretreating coal to provide solubilized coal;
bioreacting said solubilized coal with at least one type of coal-utilizing bacteria;
generating biomass and lipids from said step of bioreacting said solubilized coal with said at least one coal-utilizing bacteria; and
converting said lipids into biofuel.

Clause 1b. A method for producing biofuel from coal comprising the steps of:
bioreacting coal with at least one type of coal-utilizing bacteria;
generating biomass and lipids from said step of bioreacting said solubilized coal with said at least one coal-utilizing bacteria; and
converting said lipids into biofuel.

Clause 2. A method for producing biofuel from coal according to clause 1 or any other clause wherein said coal is selected from a group consisting of coal fines, waste coal, low grade coal, and any combination thereof.

Clause 3. A method for producing biofuel from coal according to clause 1 or any other clause wherein said step of pretreating said coal comprise the step of pretreating said coal in a coal pretreatment reactor.

Clause 4. A method for producing biofuel from coal according to clause 1 or any other clause wherein said step of pretreating said coal comprises the step of ex situ pretreating said coal.

Clause 5. A method for producing biofuel from coal according to clause 1 or any other clause wherein said step of pretreating said coal comprises the step of providing conditions for said pretreatment step selected from a group consisting of near-ambient temperatures and near-ambient pressures.

Clause 6. A method for producing biofuel from coal according to clause 1 or any other clause wherein said step of pretreating said coal comprises the step of treating said coal with a pretreatment element selected from a group consisting of at least one alkali, at least one acid, at least one solvent, at least one oxidizing agent, and any combination thereof.

Clause 7. A method for producing biofuel from coal according to clause 1 or any other clause wherein said step of pretreating said coal comprises the step of treating said coal first with at least one alkali and second treating said coal with at least one acid.

Clause 8. A method for producing biofuel from coal according to clause 7 or any other clause wherein said at least one alkali comprises NaOH and wherein said at least one acid comprises $H_2SO_4$.

Clause 9. A method for producing biofuel from coal according to clause 7 or any other clause wherein said step of treating said coal with said at least one acid comprises the step of treating said coal with said at least one acid until said treatment solution has a circum-neutral pH.

Clause 10. A method for producing biofuel from coal according to clause 3 or any other clause and further comprising the step of removing water insoluble fractions from said coal pretreatment reactor.

Clause 11. A method for producing biofuel from coal according to clause 1 or any other clause wherein said step of bioreacting said solubilized coal with said at least one type of coal-utilizing bacteria comprises the step of bioreacting said solubilized coal with said at least one type of coal-utilizing bacteria in a bioreactor.

Clause 12. A method for producing biofuel from coal according to clause 1 or any other clause wherein said at least one coal-utilizing bacteria is selected from the group consisting of oleaginous bacteria, bacteria from a genus *Rhodococcus*, bacteria from a genus *Streptomyces*, bacteria from a genus *Acinetobacter*, bacteria from a genus *Pseudomonas*, bacteria from a genus *Nocardia*, bacteria from a genus *Mycobacterium*, bacteria from a genus *Gordonia*, bacteria from a genus *Dietzi*, microorganisms that grow on coal, microorganisms that accumulate triacylglycerols, and any combination thereof.

Clause 13. A method for producing biofuel from coal according to clause 1 or any other clause wherein said at least one coal-utilizing bacteria comprises genetically modified bacteria.

Clause 14. A method for producing biofuel from coal according to clause 1 or any other clause wherein said lipids are selected from a group consisting of diacylglycerols, triacylglycerols, and a combination of diacylglycerols and triacylglycerols.

Clause 15. A method for producing biofuel from coal according to clause 1 or any other clause and further comprising the step of harvesting said biomass.

Clause 16. A method for producing biofuel from coal according to clause 15 or any other clause and further comprising the step of separating said lipids from said biomass.

Clause 17. A method for producing biofuel from coal according to clause 11 or any other clause wherein said bioreactor is selected from a group consisting of a stirred tank bioreactor and an air lift bioreactor.

Clause 18. A method for producing biofuel from coal according to clause 15 or any other clause wherein said step of harvesting said biomass comprises a step selected from a group of filtration of said biomass, centrifugation of said biomass, flotation of said biomass, and settling of said biomass.

Clause 19. A method for producing biofuel from coal according to clause 16 or any other clause wherein said step of separating said lipids from said biomass comprises a step selected from a group consisting of physically extracting said lipids from said biomass, sonication of said biomass, changing a temperature of said biomass, changing a pressure of said biomass, chemically extracting said lipids from said biomass, electrically extracting said lipids from said biomass, and any combination thereof.

Clause 20. A method for producing biofuel from coal according to clause 1 or any other clause wherein said step of converting said lipids into said biofuel comprises the step of converting said lipids into said biofuel in a biodiesel production unit.

Clause 21. A method for producing biofuel from coal according to clause 1 or any other clause wherein said step of converting said lipids into said biofuel comprises the step of converting said lipids into biofuel with a transesterification reaction.

Clause 22. A method for producing biofuel from coal according to clause 21 or any other clause and further comprising the step of adding methanol to said lipids for said transesterification reaction.

Clause 23. A method for producing biofuel from coal according to clause 21 or any other clause and further comprising the step of producing biodiesel and glycerol from said transesterification reaction.

Clause 24. A method for producing biofuel from coal according to clause 23 or any other clause and further comprising the step of collecting said biodiesel and said glycerol.

Clause 25. A method for producing biofuel from coal according to clause 23 or any other clause and further comprising the step of feeding said glycerol into anaerobic digester to produce methane.

Clause 26. A method for producing biofuel from coal according to clause 23 or any other clause and further comprising the step of utilizing said biodiesel in an element selected from a group consisting of jet fuel, fuel replacements, salable chemicals, a lipid slurry, direct fuel replacement, fuel blending agent, and any combination thereof.

Clause 27. A method for producing biofuel from coal according to clause 16 or any other clause and further comprising the step of harvesting non-lipid biomass from said separation of said lipids from said biomass.

Clause 28. A method for producing biofuel from coal according to clause 27 or any other clause and further comprising the step of utilizing said non-lipid biomass for combustion or thermochemical conversion.

Clause 29. A method for producing biofuel from coal according to clause 27 or any other clause and further comprising the step of utilizing said non-lipid biomass in an anaerobic digester.

Clause 30. A method for producing biofuel from coal according to clause 27 or any other clause and further comprising the step of generating methane from said non-lipid biomass.

Clause 31. A method for producing biofuel from coal according to clause 30 or any other clause and further comprising the step of utilizing said methane to generate energy in a coal to biofuel production system.

Clause 32. A method for producing biofuel from coal according to clause 30 or any other clause and further comprising a step selected from a group consisting of directly producing methanol from said non-lipid biomass and indirectly producing methanol from said non-lipid biomass.

Clause 33. A method for producing biofuel from coal according to clause 30 or any other clause and further comprising the step of using said methanol in said step of converting said lipids into said biofuel.

Clause 34. A method for producing biofuel from coal according to clause 27 or any other clause and further comprising a step selected from a group consisting of: recycling said non-lipid biomass for use in said step of bioreacting said solubilized coal with said at least one type of coal-utilizing bacteria; and recycling said non-lipid biomass for use in said step of pretreating said coal to provide solubilized coal.

Clause 35. A method for producing biofuel from coal according to clause 27 or any other clause and further comprising the step of converting said non-lipid biomass into an element selected from a group consisting of animal feed and aquatic feed.

Clause 36. A method for producing biofuel from coal according to clause 1 or any other clause and further comprising the step of producing minimal waste in said method.

Clause 37. A method for producing biofuel from coal according to clause 36 or any other clause wherein said minimal waste is selected from a group consisting of unreacted coal and waste water.

Clause 38a. A coal to biofuel production system comprising:
a coal pretreatment reactor having a coal input and a solubilized coal output;
a bioreactor having a solubilized coal input and a biomass output;
a biomass harvesting and separation vessel having a biomass input and a lipid output; and
a biofuel production unit having a lipid input and a biofuel output.

Clause 38b. A coal to biofuel production system comprising:
a bioreactor having a solubilized coal input and a biomass output;
a biomass harvesting and separation vessel having a biomass input and a lipid output; and
a biofuel production unit having a lipid input and a biofuel output.

Clause 39. A coal to biofuel production system according to clause 38 or any other clause wherein said coal input of said coal pretreatment reactor is configured to input coal selected from a group consisting of coal fines, waste coal, low grade coal and any combination thereof.

Clause 40. A coal to biofuel production system according to clause 38 or any other clause wherein said coal pretreatment reactor comprises a simple reactor.

Clause 41. A coal to biofuel production system according to clause 38 or any other clause wherein said coal pretreatment reactor comprises an ex situ coal pretreatment reactor.

Clause 42. A coal to biofuel production system according to clause 38 or any other clause wherein said coal pretreatment reactor comprises a treatment condition selected from a group consisting of near-ambient temperature and near-ambient pressure.

Clause 43. A coal to biofuel production system according to clause 38 or any other clause wherein said coal pretreatment reactor further comprises a pretreatment input configured to input an element selected from a group consisting of at least one alkali, at least one acid, at least one solvent, at least one oxidizing agent, and any combination thereof.

Clause 44. A coal to biofuel production system according to clause 38 or any other clause wherein said coal pretreatment reactor comprises a first alkali input and a second acid input.

Clause 45. A coal to biofuel production system according to clause 44 or any other clause wherein said alkali input comprises a NaOH input and wherein said acid input comprises a $H_2SO_4$ input.

Clause 46. A coal to biofuel production system according to clause 38 or any other clause and further comprising a insoluble fractions removal element in said coal pretreatment reactor.

Clause 47. A coal to biofuel production system according to clause 38 or any other clause wherein said bioreactor comprises at least one type of coal-utilizing bacteria.

Clause 48. A coal to biofuel production system according to clause 38 or any other clause wherein said at least one coal-utilizing bacteria is selected from the group consisting of oleaginous bacteria, bacteria from a genus *Rhodococcus*, bacteria from a genus *Streptomyces*, bacteria from a genus *Acinetobacter*, bacteria from a genus *Pseudomonas*, bacteria from a genus *Nocardia*, bacteria from a genus *Mycobacterium*, bacteria from a genus *Gordonia*, bacteria from a genus *Dietzi*, microorganisms that grow on coal, microorganisms that accumulate triacylglycerols, and any combination thereof.

Clause 49. A coal to biofuel production system according to clause 38 or any other clause wherein said at least one coal-utilizing bacteria comprises a genetically modified bacteria.

Clause 50. A coal to biofuel production system according to clause 38 or any other clause wherein said biomass harvesting and separation vessel further comprises a lipids separator.

Clause 51. A coal to biofuel production system according to clause 38 or any other clause wherein said lipid output is selected from a group consisting of a diacylglycerols output and a triacylglycerols output.

Clause 52. A coal to biofuel production system according to clause 38 or any other clause wherein said bioreactor is selected from a group consisting of a stirred tank bioreactor and an air lift bioreactor.

Clause 53. A coal to biofuel production system according to clause 38 or any other clause wherein said biomass harvesting and separation vessel comprises an element selected from a group consisting of a filtration element, a centrifugation element, a flotation element, and a settling element.

Clause 54. A coal to biofuel production system according to clause 50 or any other clause wherein said lipids separator is selected from a group consisting of a physical separator, a sonicator, a temperature changer, a pressure changer, a chemical separator, a solvent extraction, an electrical separator, and any combination thereof.

Clause 55. A coal to biofuel production system according to clause 38 or any other clause wherein said biofuel production unit comprises a methanol input.

Clause 56. A coal to biofuel production system according to clause 1 or any other clause wherein said biofuel output comprises a biodiesel output.

Clause 57. A coal to biofuel production system according to clause 38 or any other clause wherein said biofuel production unit further comprises a glycerol output.

Clause 58. A coal to biofuel production system according to clause 38 or any other clause wherein said biomass harvesting and separation vessel comprises a non-lipid biomass output.

Clause 59. A coal to biofuel production system according to clause 38 or 58 or any other clause and further comprising an anaerobic digester having a non-lipid biomass input.

Clause 60. A coal to biofuel production system according to clause 59 or any other clause wherein said anaerobic digester further comprises a glycerol input and methane output.

Clause 61. A coal to biofuel production system according to clause 60 or any other clause wherein methane from said methane output is used to generate energy in said coal to biofuel production system.

Clause 62. A coal to biofuel production system according to clause 60 or any other clause wherein said methane from said methane output is converted to methanol for input into said biodiesel production unit.

Clause 63. A coal to biofuel production system according to clause 58 or any other clause wherein said non-lipid biomass from said non-lipid biomass output is fed into said coal pretreatment reactor through a non-lipid biomass input.

Clause 64. A coal to biofuel production system according to clause 38 or any other clause wherein said biofuel production unit comprises lipid transesterification process.

Clause 65. A coal to biofuel production system according to clause 58 or any other clause wherein said non-lipid biomass from said non-lipid biomass output is fed into said bioreactor through a non-lipid biomass input.

As can be easily understood from the foregoing, the basic concepts of the present invention may be embodied in a variety of ways. It involves both biological conversion techniques as well as devices to accomplish the appropriate biological conversion. In this application, the biological conversion techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "converter" should be understood to encompass disclosure of the act of "converting"—whether explicitly discussed or not—and, conversely, were there effectively disclosure of the act of "converting", such a disclosure should be understood to encompass disclosure of a "converter" and even a "means for "converting." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed below in the reference table or in any other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

I. U.S. Patent Documents

| Pat. No. | Kind Code | Issue Date | Name of Patentee or Applicant of cited Document |
|---|---|---|---|
| 7,832,475 | US | Nov. 16, 2010 | Jin et al. |
| 8,127,839 | US | Mar. 6, 2012 | Jin et al. |
| 7,118,896 | US | Oct. 10, 2006 | Kalscheuer et al. |
| 7,556,094 | US | Jul. 7, 2009 | Urynowicz et al. |
| 7,709,624 | US | May 4, 2010 | Nakashima et al. |
| 7,832,475 | US | Nov. 16, 2010 | Jin et al. |
| 8,127,839 | US | Mar. 6, 2012 | Jin et al. |
| 8,268,610 | US | Sep. 18, 2012 | Franklin et al. |
| 8,633,012 | US | Jan. 21, 2014 | Franklin et al. |

II. U.S. Patent Application Publications

| Publication Number | Kind Code | Publication Date | Name of Patentee or Applicant of cited Document |
|---|---|---|---|
| 20070022122 | A2 | Feb. 22, 2007 | Jin et al. |
| 20060172423 | A1 | Aug. 3, 2006 | Van Der Geize et al. |
| 20090193712 | A1 | Aug. 6, 2009 | Verkade et al. |
| 20100081178 | A1 | Apr. 1, 2010 | Roberts et al. |
| 20100257778 | A1 | Oct. 14, 2010 | Gaertner et al. |
| 20110146142 | A1 | Jun. 23, 2011 | Lee et al. |
| 20110244532 | A1 | Oct. 6, 2011 | Hu et al. |
| 20120110898 | A1 | May 10, 2012 | Malm et al. |
| 20120142979 | A1 | Jun. 7, 2012 | Keasling et al. |
| 20120244585 | A1 | Sep. 27, 2012 | Kale et al. |
| 20120247763 | A1 | Oct. 4, 2012 | Rakitsky et al. |
| 20120264983 | A1 | Oct. 18, 2012 | Hu et al. |
| 20130137887 | A1 | May 30, 2013 | Kurosawa et al. |

III. Foreign Patent Documents

| Foreign Document Number | Country Code | Kind Code | Publication Date | Name of Patentee or Applicant of cited Document |
|---|---|---|---|---|
| 2025755 | EP | A1 | Feb. 18, 2009 | Ros |
| 2007022122 | WO | A2 | Feb. 22, 2007 | Jin et al. |
| 2008151149 | WO | A2 | Dec. 11, 2008 | Trimbur et al. |
| 2010120939 | WO | A2 | Oct. 21, 2010 | Wittenberg et al. |
| 2011071553 | WO | A1 | Jun. 16, 2011 | Downey et al. |
| 2011075163 | WO | A1 | Jun. 23, 2011 | Downey et al. |
| 2011133218 | WO | A1 | Oct. 27, 2011 | Downey |
| 2012154329 | WO | A1 | Nov. 15, 2012 | Greenfield et al. |
| 2013082309 | WO | A1 | Jun. 6, 2013 | Reed et al. |
| 2013177471 | WO | A2 | Nov. 28, 2013 | Urynowicz et al. |

IV. Non-Patent Literature Documents

Schulz, H., Short history and present trends of Fischera €.Tropsch synthesis. Applied Catalysis A: General, 1999. 186 (1a €.2): p. 3-12.

Höök, M. and K. Aleklett, A review on coal-to-liquid fuels and its coal consumption. International Journal of Energy Research. 34(10): p. 848-864.

Dry, M. E., The Fischera €.Tropsch process: 1950a €.2000. Catalysis Today, 2002. 71(3a €.4): p. 227-241.

Bellman, D. K., Coal to Liquids and Gas 2007, National Petroleum Council.

Cicero, D. C., Coal-to-Liquids in the United States Status and Roadmap, in CTLtec Americas 2008. 2008, Department of Energy National Energy Technology Laboratory.

NYMEX. Monthly Commodity Futures Price Chart. 2012 [cited 2012 Apr. 4, 2012]; Available from: http://futures.tradingcharts.com/chart/CO/M.

Fakoussa, R. M. and M. Hofrichter, Biotechnology and microbiology of coal degradation. Applied Microbiology and Biotechnology, 1999. 52(1): p. 25-40.
Catcheside, D. E. A. and J. P. Ralph, Biological Processing of Coal. Appl. Microbiol Biotechnol, 1999. 52: p. 16-24.
Gruver, M., Microbes may produce marketable methane gas from old coal, in USA Today. 2011, Associated Press: Gillette, WY.
Li, Q., W. Du, and D. Liu, Perspectives of microbial oils for biodiesel production. Applied Microbiology and
Biotechnology, 2008. 80(5): p. 749-756.
Jin, S. and A. E. Bland, Formation Pretreatment with Biogenic Methane Production Enhancement Systems, USPTO, Editor. 2011, University of Wyoming Research Corporation d/b/a Western Research Institute: US.
Verkade, J. G., R. E. Oshel, and R. A. Downey, Pretreatment of Coal, USPTO, Editor. 2009, Ciris Energy: United State.
DeBruyn, R. P., et al., Generation of Hydrogen from Hydrocarbon Bearing Materials, USPTO, Editor. 2012, Luca Technologies, Inc.: United States. p. 15.
Demirbas, A., Characterization of Biodiesel Fuels. Energy Sources, Part A: Recovery, Utilization, and Environmental Effects, 2009. 31(11): p. 889-896.
Alvarez, H. A. and A. S. Steinbüchel, Triacylglycerols in prokaryotic microorganisms. Applied Microbiology and
Biotechnology, 2002. 60(4): p. 367-376.
Holder, J. W., et al., Comparative and Functional Genomics of *Rhodococcus opacus* PD630 for Biofuels Development. PLOS Genet. 7(9): e1002219. 2011.
Füchtenbusch, B. and A. Steinbüchel, Biosynthesis of polyhydroxyalkanoates from low-rank coal liquefaction products by & lt;i& gt; *Pseudomonas oleovorans* & lt;/i& gt;
and & lt;i& gt; *Rhodococcus* ruber & lt;/i& gt. Applied Microbiology and Biotechnology, 1999. 52(1): p. 91-95.
U.S. Provisional Patent Application No. 61/783,103 filed Mar. 14, 2013, "Biological Methods and Systems for Coal-to-Biofuel and Bioproducts"
DOE/NETL. "Affordable, Low-Carbon Diesel Fuel from Domestic Coal and Biomass." 2009. DOE/NETL-2009/1349 report. Jan. 14, 2009.

Thus, the applicant(s) should be understood to have support to claim and make a statement of invention to at least: i) each of the biological conversion devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC*, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A method for producing biofuel from coal comprising the steps of:
   pretreating coal first with an alkali comprising NaOH and second with an acid comprising $H_2SO_4$ to provide solubilized coal;
   removing water insoluble fractions from said solubilized coal;
   bioreacting said solubilized coal with at least one type of coal-utilizing bacteria;
   generating biomass and lipids from said step of bioreacting said solubilized coal with at least one type of coal-utilizing bacteria;
   converting said lipids into biodiesel with a transesterification reaction in a biodiesel production unit;
   producing biodiesel and glycerol from said transesterification reaction;
   collecting said biodiesel and glycerol;
   anaerobically digesting excess biomass that cannot be converted into biodiesel;
   producing methane from said step of anaerobically digesting said excess biomass; and
   adding at least some of said glycerol to said step of anaerobically digesting said excess biomass.

2. The method for producing biofuel from coal according to claim 1 wherein said coal is selected from a group consisting of coal fines, waste coal, and any combination thereof.

3. The method for producing biofuel from coal according to claim 1 wherein said at least one coal-utilizing bacteria comprises genetically modified bacteria capable of bioreacting said solubilized coal.

4. The method for producing biofuel from coal according to claim 1 wherein said lipids are selected from a group consisting of diacylglycerols, triacylglycerols, and a combination of diacylglycerols and triacylglycerols.

5. The method for producing biofuel from coal according to claim 1 and further comprising a step of feeding said glycerol into an anaerobic digester to produce methane.

6. The method for producing biofuel from coal according to claim 1 and further comprising producing waste in said method wherein said waste is selected from a group consisting of unreacted coal and waste water.

7. The method for producing biofuel from coal according to claim 1 wherein said step of bioreacting said solubilized coal with said at least one coal-utilizing bacteria comprises a step of ex-situ bioreacting said solubilized coal with said at least one coal-utilizing bacteria.

8. The method for producing biofuel from coal according to claim 1 wherein said step of pretreating coal to provide solubilized coal comprises a step of in-situ pretreating coal to provide solubilized coal.

9. The method for producing biofuel from coal according to claim 1 wherein said coal-utilizing bacteria comprises a member of a genera selected from a group consisting of *Rhodococcus, Streptomyces, Acinetobacter, Pseudomonas, Nocardia, Myca* bacterium, *Gordonia, Dietzi*, and any combination thereof.

10. The method for producing biofuel from coal according to claim 1 wherein said coal-utilizing bacteria comprises bacteria from the genus *Rhodococcus*.

* * * * *